United States Patent [19]
Qu et al.

[11] Patent Number: 5,969,231
[45] Date of Patent: *Oct. 19, 1999

[54] SENSOR FOR MONITORING CONCENTRATION OF GASEOUS SUBSTANCES

[75] Inventors: Wenmin Qu, Dresden; Jörg-Uwe Meyer, St. Ingbert, both of Germany

[73] Assignee: Fraunhofer Gesellschaft zur Foedering der Angewandten Forschung e.V., Germany

[*] Notice: This patent issued on a continued prosecution application filed under 37 CFR 1.53(d), and is subject to the twenty year patent term provisions of 35 U.S.C. 154(a)(2).

[21] Appl. No.: 08/832,315

[22] Filed: Mar. 17, 1997

Related U.S. Application Data

[63] Continuation-in-part of application No. PCT/EP95/03547, Sep. 8, 1995.

[30] Foreign Application Priority Data

Sep. 16, 1994 [DE] Germany ............................. 44 33 102

[51] Int. Cl.⁶ .................................................. G01N 27/12
[52] U.S. Cl. ........................... 73/31.05; 73/31.06; 338/34
[58] Field of Search ................................. 73/23.2, 23.31, 73/23.34, 31.01, 31.02, 31.03, 31.06; 338/34, 35

[56] References Cited

U.S. PATENT DOCUMENTS

| | | | |
|---|---|---|---|
| 3,255,324 | 6/1966 | Ovshinsky | 338/34 X |
| 3,705,375 | 12/1972 | Hershler | 338/35 |
| 4,328,478 | 5/1982 | Murata et al. | 73/335.05 X |
| 4,377,944 | 3/1983 | Hishii et al. | 73/31.06 |
| 4,422,129 | 12/1983 | Briant et al. | 338/35 X |
| 4,447,352 | 5/1984 | Inoue et al. | 338/35 X |
| 4,464,647 | 8/1984 | Yokomizo et al. | 73/335.05 X |
| 5,618,496 | 4/1997 | Hasumi et al. | 73/31.06 X |

*Primary Examiner*—Michael Brock
*Attorney, Agent, or Firm*—Evenson, McKeown, Edwards & Lenahan, P.L.L.C.

[57] ABSTRACT

The invention provides a sensor arrangement for monitoring the concentration of moisture and gaseous substances in ambient air. A gas sensitive intermediate layer is sandwiched between top and bottom electrodes, each of which comprises first and second interdigitated conductive elements, which are coupled to an opposite polarity voltage. The top and bottom electrodes are super-imposed on opposite sides of the gas-sensitive intermediate layer, with fingers of the top electrode having a voltage polarity which is opposite that of adjacent super-imposed fingers of the bottom electrode.

4 Claims, 3 Drawing Sheets

TOP ELECTRODE

BOTTOM ELECTRODE

SENSOR FOR MONITORING CONCENTRATION OF GASEOUS SUBSTANCES

This application is a continuation in part of International Application PCT/EP 95/03547, filed Sep. 8, 1995, designating the United States and other countries.

BACKGROUND AND SUMMARY OF THE INVENTION

The present invention relates to a sensor for monitoring the concentration of moisture and gaseous substances in the air.

In order to provide and ensure a healthy, comfortable and safe environment for both humans and machines, air conditioners and air purifiers are needed to improve the quality of ventilation. Sensor technology serving as feedback in the automatic control of the air channels is important for continuous assessment and monitoring of temperature, moisture and gaseous toxic substances.

Measuring systems of a high technical standard and reliability are already available for the determination of the humidity and gas concentration of the air. These include psychometers or dew point measuring devices for determining humidity and gas chromatography or IR-spectrometry for determining the concentration of gas. However, for economical and handling reasons, and in particular due to their complexity, these laboratory devices are not suited for monitoring in air conditioning systems. In order to determine the humidity and gas concentration in the air in a simpler and less expensive manner, various compact, ceramic sensor elements made of semiconductive metal oxides such as $Al_2O_3$, $TiO_2$—$V_2O_5$, $MgAl_2O_4$, $M_NWO_4$, $MgFe_2O_4$, $ZnCr_2O_4$—$LiZnVO_4$ or $MgCr_2O_4$—$TiO_2$ were developed for moisture sensors and of $SnO_2$, $ZnO$, $TiO_2$, $WO_3$, $Fe_2O_3$, $LaNiO_2$, $CoO$ or $PtO_2$ for gas sensors. Despite their more or less major drawbacks, these sensor systems find use in numerous practical applications.

High sensitivity, large measurement range, short response times and small size are the most important requirements for a gas sensor element. Some of these requirements are mutually compatible. However, some of them conflict with each other, making development of an ideal sensor especially difficult.

Gas sensors of the generic type described above utilize the phenomenon of adsorption of water vapor or of the various gases on the surface of a semiconductive metal oxide, which alters the physical properties of the metal oxide, in particular, its surface conductivity. Known $SnO_2$ gas sensor are based, for example, on the phenomenon that removal of the oxygen ions adsorbed on the $SnO_2$ surface lowers the electrical resistance of the sensor under the influence of the reducing gases. The moisture sensor is based on the principle that the resistance of many metal oxides changes logarithmically with increasing humidity. By measuring the changes in electric resistance of the metal oxide under the influence of moisture or various gases, the air moisture or gas concentration can be determined.

It is known, however, that the sensitivity of a sensor depends not only on properties of the sensitive material itself, but also on the measurement method used to determine the change in such properties. Thus, the shape of the electrical contacts ("meter electrodes") plays an important role in the effective detection of the sensor signal. The resistance of the metal oxide diminishes following the absorption of the water molecules or the reducing gases. In order to assess these changes (and thus to determine the moisture content or the gas concentration of the surroundings), two different meter electrode arrangements are presently employed in thick-film technology. Each of these arrangements has its advantages and disadvantages.

FIG. 1 shows the buildup of a prior art sensor having planar interdigitated electrodes, such as is disclosed, for example, in O. Niwa et al., Anal. Chem. 62, 1990, 447–452. First the interdigitated electrode is printed onto an $AL_2O_3$ substrate by means of serigraphy. Then this structure is dried at room temperature and baked in an oven at high temperatures. Subsequently, the paste composed of the sensitive metal oxides is pressed onto the previously baked electrode and dried or baked.

This sensor element constructed as a planar interdigitated capacitor has the advantage that the components which are to be detected are able to reach the sensitive layer directly without encumbrance, because the finger-shaped (interdigitated) electrode arrangement is located under this active layer. Therefore this sensor has a short response time. However, a disadvantage of this type of sensor is its high internal resistance, which diminishes its sensitivity. Especially in the low water vapor or gas concentration range, the changes in the sensor resistance do not follow the concentration changes of the detected components sensitively enough. This sensor element is therefore predominantly employed in either relatively high concentration ranges or in cases in which only rapid response behavior is required.

In order to improve the sensor sensitivity, particularly in low water vapor or gas concentrations, it is necessary to reduce the internal resistance of the sensor. For this purpose, gas sensors are known, which have a "sandwich" configuration, in which the two plate electrodes are disposed parallel to each other and the intermediate space is filled with the active layer, as shown in FIG. 2. In the thick-film process, the sensor element is built up on an $AL_2O_3$ substrate in three printing procedures as follows: the bottom plate electrode, sensor layer and top plate electrode. After printing each layer, it is dried at room temperature and subsequently baked at high temperatures.

With this configuration, and gas sensor has a low interior resistance and can therefore achieve high sensitivity even in low water vapor or gas concentrations. Because of the two large plate electrodes, it measures via a very thin active layer. However, due to the given technological conditions, despite the close mesh sieve only electrodes having layer thickness greater than the micron range can be produced in the layer thickness process. Due to the fact that the water molecules or the gas molecules first have to penetrate the thick, whole surface cover electrode in order to reach to reach the active layer, the sensor element has a long response time.

One object of the present invention, therefore, is to provide a sensor arrangement which achieves a high sensitivity, and at the same time has large measurement range, with a short response time.

Another object of the invention is to provide a sensor which achieves these goals, and is also compact.

The sensor arrangement according to the present invention accomplishes the objects described above by utilizing a "sandwich" configuration, in which a substantially planar sensitive layer is disposed between two "plates", each of which has an interdigitated structure, with opposed fingers of the interdigitated structure having an opposite polarity. This design of the electrodes results in a reduced internal resistance of the sensor, so that the sensor according to the invention possesses high sensitivity, even in the case of low concentrations of the components which are to be detected. Since the interdigitated structure does not entirely cover the surface of the sensitive layer, this arrangement also allows gas or water molecules to reach the active layer directly, thereby shortening its response time. Accordingly, a compact sensor arrangement is achieved, which has a short response time and a high sensitivity.

Other objects, advantages and novel features of the present invention will become apparent from the following detailed description of the invention when considered in conjunction with the accompanying drawings.

DETAILED DESCRIPTION OF THE DRAWINGS

The new electrode arrangement for contacting the gas sensor combines the advantage of both interdigitated electrodes and plate electrodes. As a consequence, the gas sensor according to the invention possesses high sensitivity even at low concentration of the to-be detected components. In addition, it has a large measurement range and its response time is shortened.

The gas sensor according to the invention has a "sandwich" configuration. What is special, however, is that each of the "plates" has an interdigitated structure, with the voltage polarity of oppositely disposed finger structures being intentionally reversed. In this configuration, each electrode taken individually is an interdigitated capacitor, creating again a plate capacitor between the top and bottom electrode by means of the opposite voltage polarity.

Figure 1:
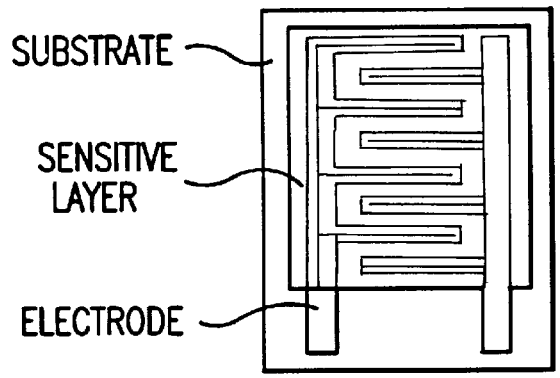
FIG. 1 shows the construction of a prior art sensor having planar interdigitated electrodes.
Figure 2:
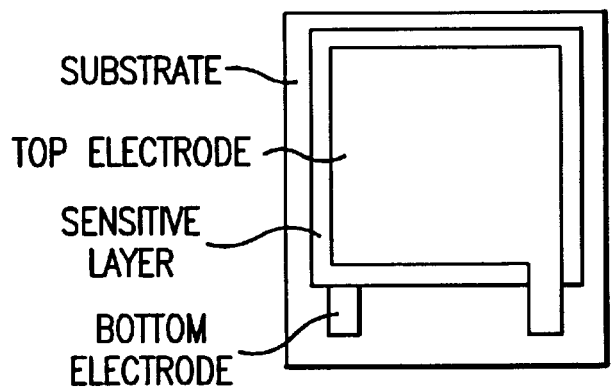
FIG. 2 shows the construction of a thick film gas sensor having a sensitive layer sandwiched between plate electrodes.
Figure 3A:
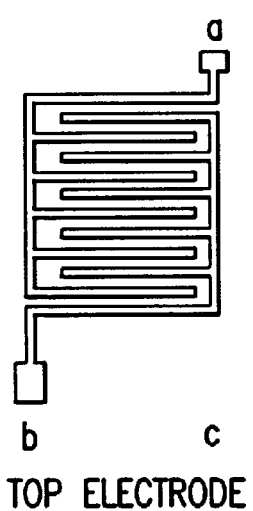
FIG. 3 shows the design of the electrode plates in the sensor according to the invention.
Figure 3B:
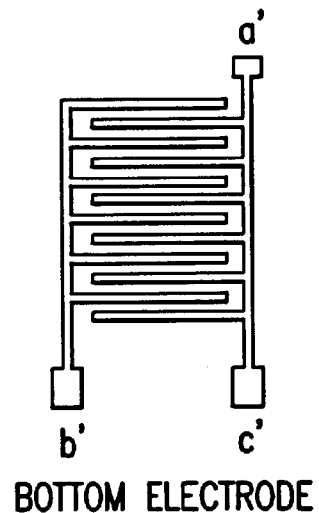

FIG. 3 shows the design of the two electrodes in the sensor according to the invention. Due to the serigraphy processes, the two electrodes will lie precisely superimposed, which can cause an electric short circuit between the two electrodes in the area which is not insulated by the intermediate active layer. Therefore, points a and a' as well as b and b' are connected and thus have the same potential. Superpositioning of the electrodes thus yields the necessary opposite voltage polarities.

Figure 4A:
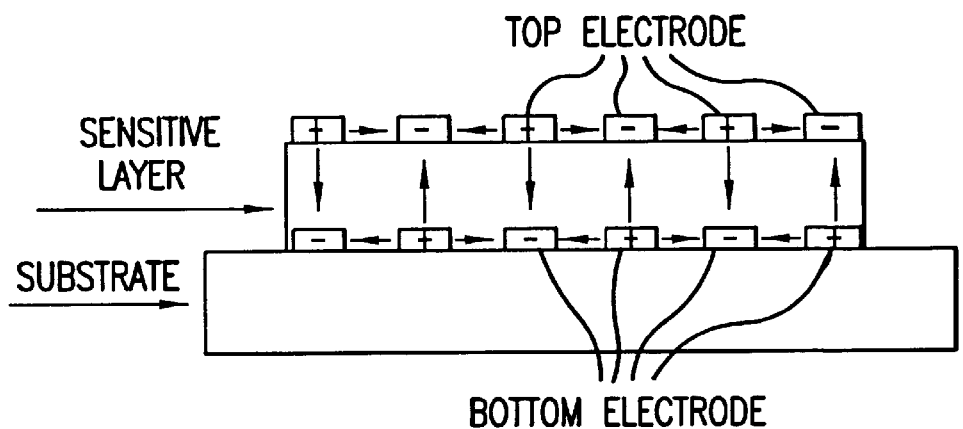
FIG. 4a shows a cross-sectional view of the thick film gas sensor according to the invention.
Figure 4B:
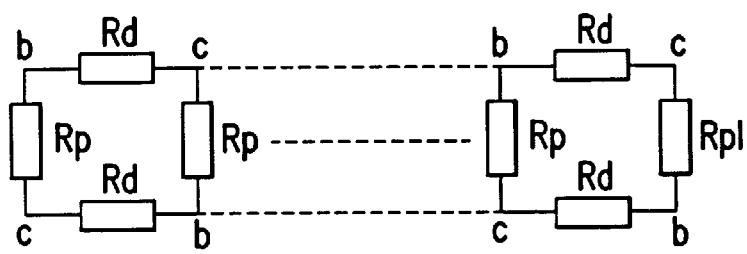
FIGS. 4b and c show equivalent circuit representations of the gas sensor according to the invention.
Figure 4C:
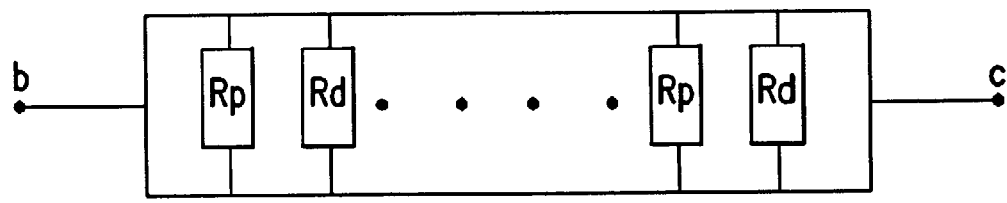

As shown in cross section in FIG. 4a, this structure thus represents a three-dimensional capacitor in which the two electrodes are coupled counter each other in parallel, and are themselves interdigitated capacitively. The design of the "interdigitated sandwich" electrode arrangement permits optimum utilization of the sensitive layer, which simultaneously permits a reduction in the size of the sensor element. Each single electrode finger forms with its adjacent fingers either a plate capacitor or an interdigitated capacitor. Electrical changes in the active layer are thereby evaluated more effectively in the interdigitated and plate capacitors connected in parallel. The overall sensor resistance $R_{bc}$ is described by the following equation, based on the equivalent circuit configurations of FIGS. 4b and 4c:

$$\frac{1}{R_{bc}} = \frac{1}{R_p} * n + \frac{1}{R_d} * 2(n-1)$$

$R_p$=the resistance, of the fingers separated by the sensitive layer in space;

$R_d$=the resistance between the fingers in the plane;

n=the number of fingers.

The altered design of the electrodes according to the invention results in a reduced internal resistance of the sensor. For this reason, the sensor possesses high sensitivity, even in low concentrations of the components which are to be detected. The top interdigitated electrode, which is not fully closed as can be seen in FIG. 3, permits the water or gas molecules to reach the active layer directly, thereby shortening its response time. The advantages of both the interdigitated electrodes and plate electrodes are thus combined in this electrode arrangement.

Table 1 shows a comparison of the internal resistances and the respective response times of the three different electrode arrangements, determined in a series of tests. Thick-film moisture sensors having 40 $\mu$m thick polycrystalline MnWO$_4$ layers were used for this measurement, with the different electrode arrangements. The advantage of the newly developed electrode arrangement is distinctly shown by the results in this table.

| Internal Resistance and Response Times for Indicated Electrode Configurations | | | |
| --- | --- | --- | --- |
| Electrode Configuration | Internal Resistance | Rise Time (sec) | Fall Time (sec.) |
| Interdigital | 20,000.00 | 3–5 | 4–7 |
| Parallel | 0.5 | 123 | 170 |
| Invention | 0.8 | 3–5 | 5–9 |

Figure 5:
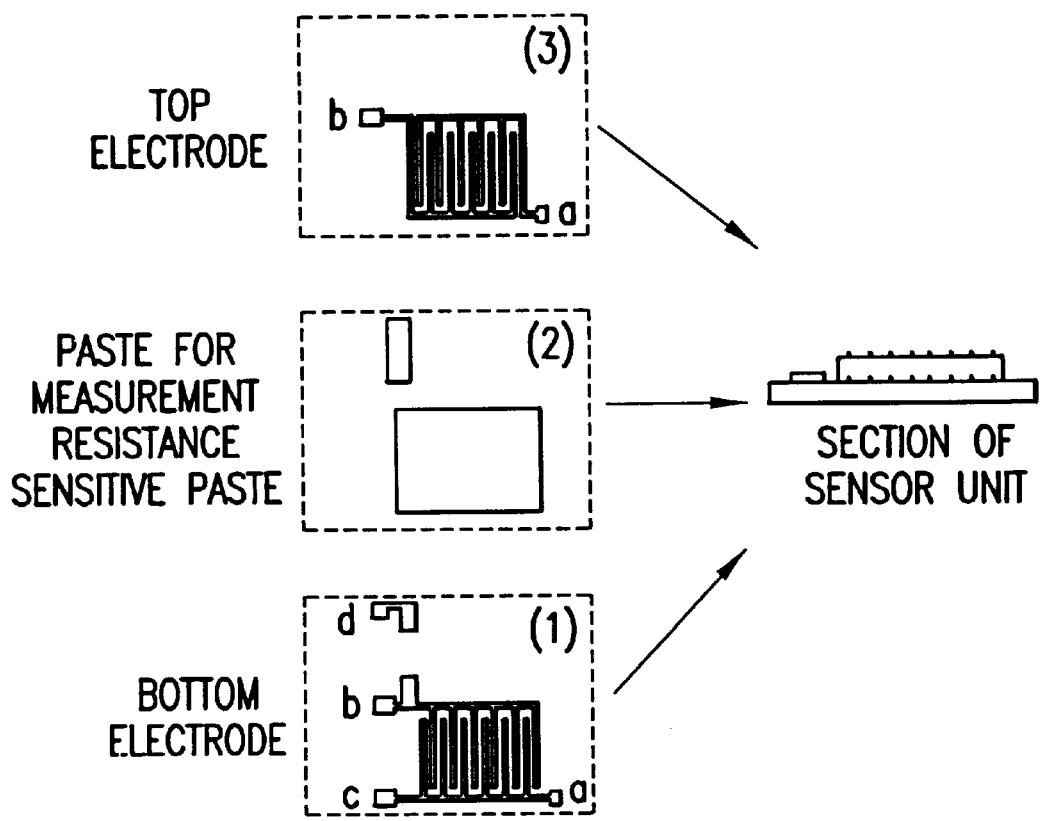
FIG. 5 illustrates the construction and printing process of the sensor unit according to the invention.

To complete the sensor element, a measurement resistance is also printed with the sensor electrodes, as shown in FIG. 5. The result is a sensor unit in which the bottom electrodes serve both as sensor electrodes and as a contact bed for the measurement resistance.

The procedure for fabricating the sensor is as follows:

1. The bottom electrode of platinum or gold paste is printed onto an Al$_2$O$_3$-substrate. The print is dried and baked. (FIG. 5(a))

2. Then the sensitive paste is printed onto the already baked bottom electrode, as shown in FIG. 5(b). After drying of the printed sensor paste, the procedure is repeated. In this way, the desired layer thickness is raised and a closed surface is created. When the second paste layer is also dried, the paste for the measurement resistance is printed on and dried.

3. Finally, the top electrode is printed on the sensor, as shown in FIG. 5(c). When the paste of the top electrode is dry, the two last printed pastes are baked together (co-firing).

Figure 6:
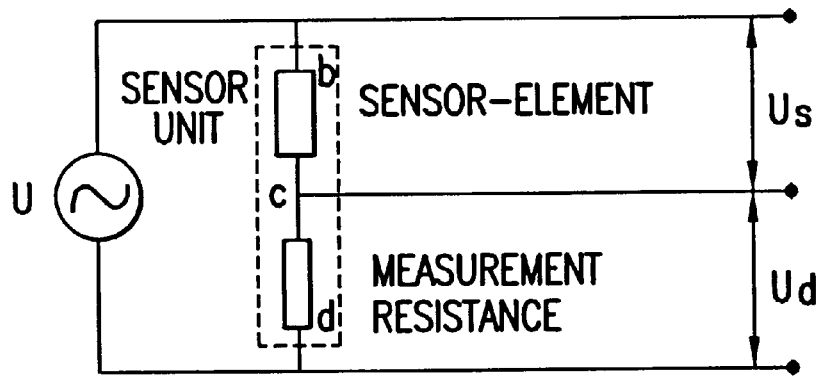
FIG. 6 shows a circuit for triggering and readout of the gas sensor according to the invention.

This sensor unit simplifies evaluating the sensor signal; only one external voltage is required. The measurement circuit is shown in FIG. 6. The drop in voltage at the measurement resistance is evaluated as the sensor signal.

The sensor according to the invention may be utilized in all applications in which a thick-film gas sensor is required to possess high sensitivity as well as a rapid response time, including:

Monitoring ventilation,

Air conditioning,

Air purifiers,

Green houses.

A preferred embodiment of the chemical sensor according to the invention is fabricated according to FIG. 5, with polycrystalline $MnWO_4$ employed as the sensitive layer. After drying and baking, the sensitive layer has a thickness of 40 μm. The width is approximately 100–300 μm. The electrodes are made of a platinum or gold compound.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A sensor for determining concentration of gaseous substances, comprising:

a gas sensitive intermediate layer sandwiched between top and bottom electrodes; wherein each of said top and bottom electrodes comprises first and second interdigitated conductive fingers having respective first and second contacts which are connected to opposite polarity voltages;

said top and bottom electrodes are superimposed on opposite sides of said intermediate layer;

fingers of said top electrode are aligned in registration with fingers of said bottom electrode, forming registered pairs of oppositely disposed fingers; and in each registered pair of fingers, a finger of said top electrode has a voltage polarity which is opposite that of an oppositely disposed finger of said bottom electrode.

2. Sensor according to claim 1 wherein said first and second contacts of said top electrode are superimposed adjacent said first and second contacts of said bottom electrode.

3. Sensor according to claim 1, further comprising a measuring resistance connected to said electrodes for measuring a voltage drop across said measuring resistance as an output of said sensor.

4. Sensor according to claim 1, wherein said sensor comprises a substrate made of $Al_2O_3$, and said electrodes are made from a material selected from the group consisting of platinum and gold.

* * * * *